United States Patent
Zhu et al.

(10) Patent No.: US 6,403,382 B1
(45) Date of Patent: Jun. 11, 2002

(54) ATTACHMENT CHEMISTRY FOR ORGANIC MOLECULES TO SILICON

(75) Inventors: Xiaoyang Zhu, Maple Grove, MN (US); Hongjun Yang, Germantown, MD (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/456,556

(22) Filed: Dec. 8, 1999

Related U.S. Application Data

(60) Provisional application No. 60/155,646, filed on Sep. 24, 1999, provisional application No. 60/111,727, filed on Dec. 10, 1998, and provisional application No. 60/111,376, filed on Dec. 8, 1998.

(51) Int. Cl.$^7$ ............................ G01N 33/68; B05D 1/36
(52) U.S. Cl. .......................... 436/176; 436/86; 427/414
(58) Field of Search ................................ 427/212, 414; 435/174, 176; 436/86, 176

(56) References Cited

U.S. PATENT DOCUMENTS

| | | | | |
|---|---|---|---|---|
| 3,303,085 A | | 2/1967 | Price et al. .................. | 161/109 |
| 4,847,159 A | * | 7/1989 | Glajch et al. ................ | 428/447 |
| 4,904,632 A | * | 2/1990 | Pesek et al. ................. | 502/158 |
| 5,429,708 A | | 7/1995 | Linford et al. ............... | 216/66 |
| 5,482,867 A | * | 1/1996 | Barrett et al. ............... | 436/518 |
| 5,843,767 A | | 12/1998 | Beattie ....................... | 435/287 |
| 5,908,692 A | | 6/1999 | Hamers et al. .............. | 428/333 |
| 5,976,896 A | * | 11/1999 | Kumar et al. ............... | 436/527 |

FOREIGN PATENT DOCUMENTS

WO  95/21030  8/1995

OTHER PUBLICATIONS

Linford et al.; "Alkyl Monolayers on Silicon Prepared from 1–Alkenes and Hydrogen–Terminated Silicon"; Journal of the American Chemistry Society; vol. 117, No. 11; 1995; pp. 3145–3155. (no mo.).

Linford et al.; "Alkly Monolayers Covalently Bonded to Silicon Surfaces"; Journal of the American Chemistry Society; vol. 115, No. 26; 1993; pp. 12631–12632. (no mo.).

Bansal et al.; "Alkylation of Si Surfaces Using a Two–Step Halogenation/Grignard Route"; Journal of the American Chemistry Society; vol. 118, No. 30; 1996; pp. 7225–7226. (no mo.).

He et al.; "Covalent Bonding of Thiophenes to Si(111) by a Halogenation/Thienlation Route"; Chemical Physics Letters; vol. 286, No. 5,6; Apr. 17, 1998; pp. 508–514.

Kim et al.; "Improved Polypyrrole/Silicon Junctions by Surfacial Modification of Hydrogen–Terminated Silicon Using Organolithium Reagents"; Journal of the American Chemistry Society; vol. 121, No. 30; 1999; pp. 7162–7163. (no mo.).

(List continued on next page.)

*Primary Examiner*—Shrive P. Beck
*Assistant Examiner*—Michael Cleveland
(74) *Attorney, Agent, or Firm*—Blank Rome Comiskey & McCauley

(57) ABSTRACT

A simple chemical approach for the covalent assembly of organic molecules on silicon surfaces via robust linkages is provided. This is achieved by the efficient reaction between a nucleophilic functional group and a halogenated Si surface. The nucleophile anchor is the bridge between two surface Si atoms. The resulting organic layer is thermally stable. The method demonstrated herein is generally applicable for the assembly of a variety of functional organic molecules under vacuum environment or in solution phase.

20 Claims, 12 Drawing Sheets

OTHER PUBLICATIONS

Hovis et al.; "Structure and Bonding of Ordered Organic Monolayers of 1,5–Cyclooctadiene on the Silicon (001) Surface"; The Journal of Physical Chemistry B; vol. 101, No. 46; Nov. 13, 1997; pp. 9581–9585.

Kugler et al.; "Chemically Modified Semiconductor Surfaces: 1,4–Phenylenediamine on Si(100)"; Surface Science; vol. 260; 1992; pp. 64–74. (no mo.).

Glass et al.; "Reaction of Methanol with Porous Silicon"; Surface Science; vol. 338; 1995; pp. 125–137. (no mo.).

Fodor et al.; "Light–Directed, Spatially Addressable Parallel Chemical Synthesis"; Science; vol. 251; Feb. 15, 1991; pp. 767–773.

Southern et al.; "Analyzing and Comparing Nucleic Acid Sequences by Hybridization to Arrays of Oligonucleotides: Evaluation Using Experimental Models"; Genomics; vol. 13; 1995; pp. 1008–1017. (no mo.).

Eggers et al.; "Genosensors: Microfabricated Devices for Automated DNA Sequence Analysis"; Progress in Biomedical Optics; vol. 1891; 1993; pp. 113–126. (no mo.).

Beattie et al.; :Genosensor Technology; Clinical Chemistry; vol. 39, No. 4; 1993; pp. 719–722. (no mo.).

Lehmann; "The Physics of Macropore Formation in Low Speed Doped n–Type Silicon"; Journal of Electrochemical Society; vol. 140, No. 10; Oct. 1993; pp. 2836–2843.

Lehmann et al.; "A new Capacitor Technology Based on Porous Silicon"; Materials; 1995; pp. 99–102. (no mo.).

Gruning et al.; "Macroporous Silicon with A Complete Two–Dimensional Photonic Band Gap Centered at 5 $\mu$m"; American Institute of Physics; vol. 68, No. 6; Feb. 5, 1996; pp. 747–479.

Lehmann et al.; "The Limits of Macropore Array Fabrication"; Thin Solid Films; vol. 297; 1997; pp. 13–97. (no mo.).

Cleland et al.: "Direct Functionalization of Silicon via the Self–assembly of Alcohols", J. Chemistry Society Trans.; vol. 19, No. 21; 1995; pp. 4001–4003. (no mo.).

Effenberger et al.: Photoactivated Preparation and Patterning of Self–Assembled Monolayers with 1–Alkenes and Aldehydes on Silicon Hydride Surfaces; vol, 37 No. 18; 1998; pp. 2462–2464. (no. mo.).

Villeneuve et al., Electrochemical Formation of Close–Packed Phenyl Layers on Si(111), J. Phys. Chem. B; vol. 101, pp. 2415–2420. 1997 (no mo.).

Lee et al.; "Light–Induced Reactions of Porous and Single–Crystal Si Surfaces with Carboxylic Acids", J. American Chem. Soc.; vol. 118; 1996; pp. 5375–5382. (no mo.).

Teplyakov, et al.; "Vibrational Spectroscopic Studies of Diels–Alder Reactions with the Si(100)–2x1 Surface as a Dienophile", J. Am. Chemistry Society; vol. 119; 1997; pp. 11100–11101. (no mo.).

* cited by examiner

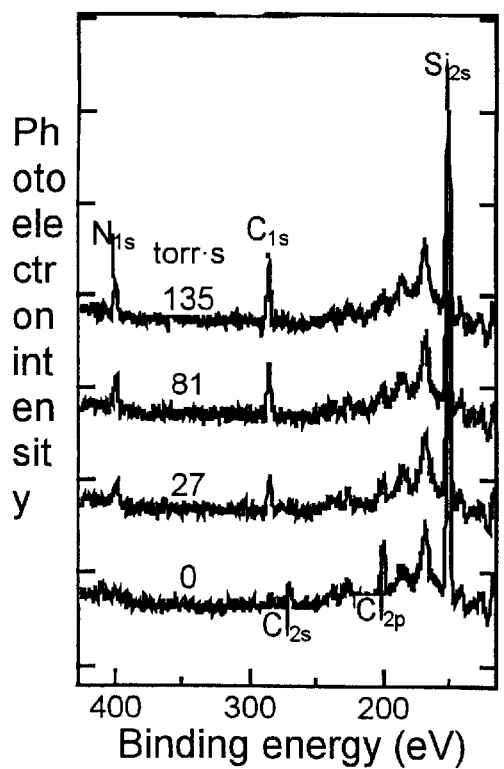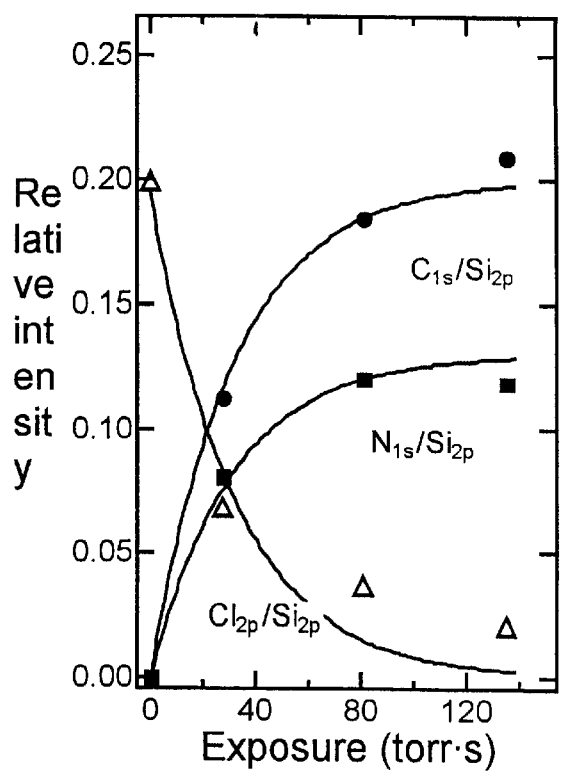
Fig. 3A
Fig. 3B

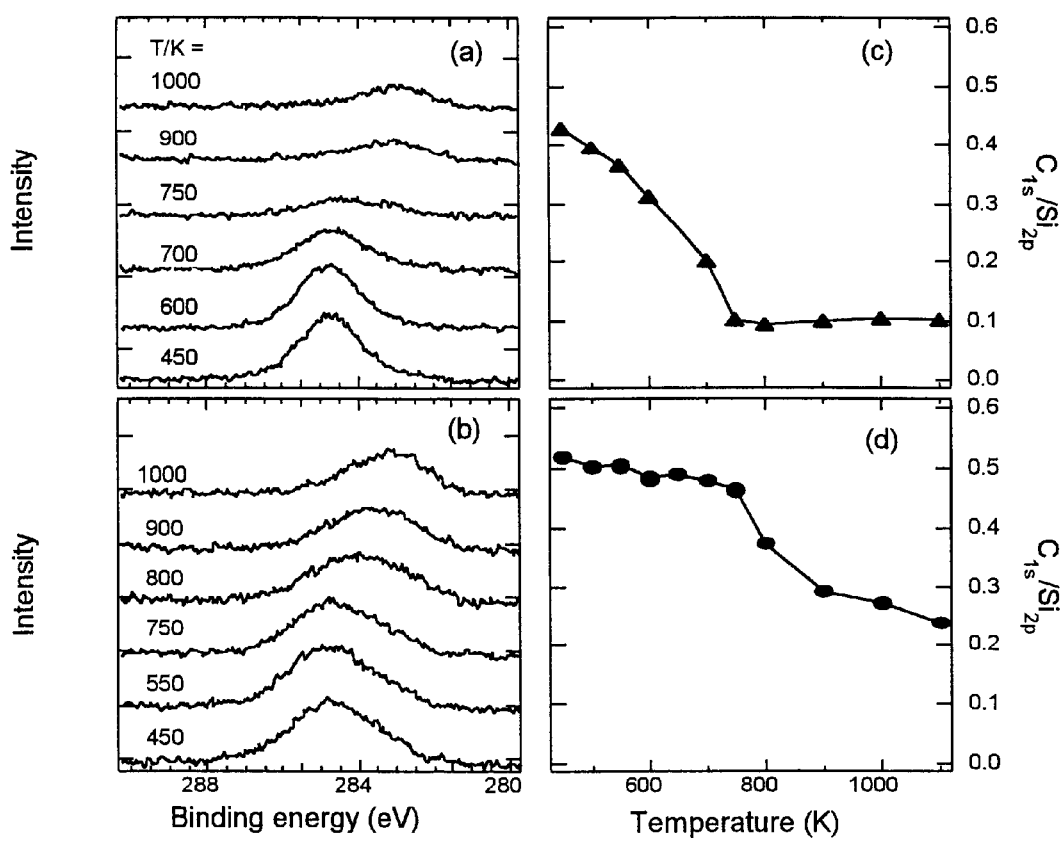
Fig. 6.0

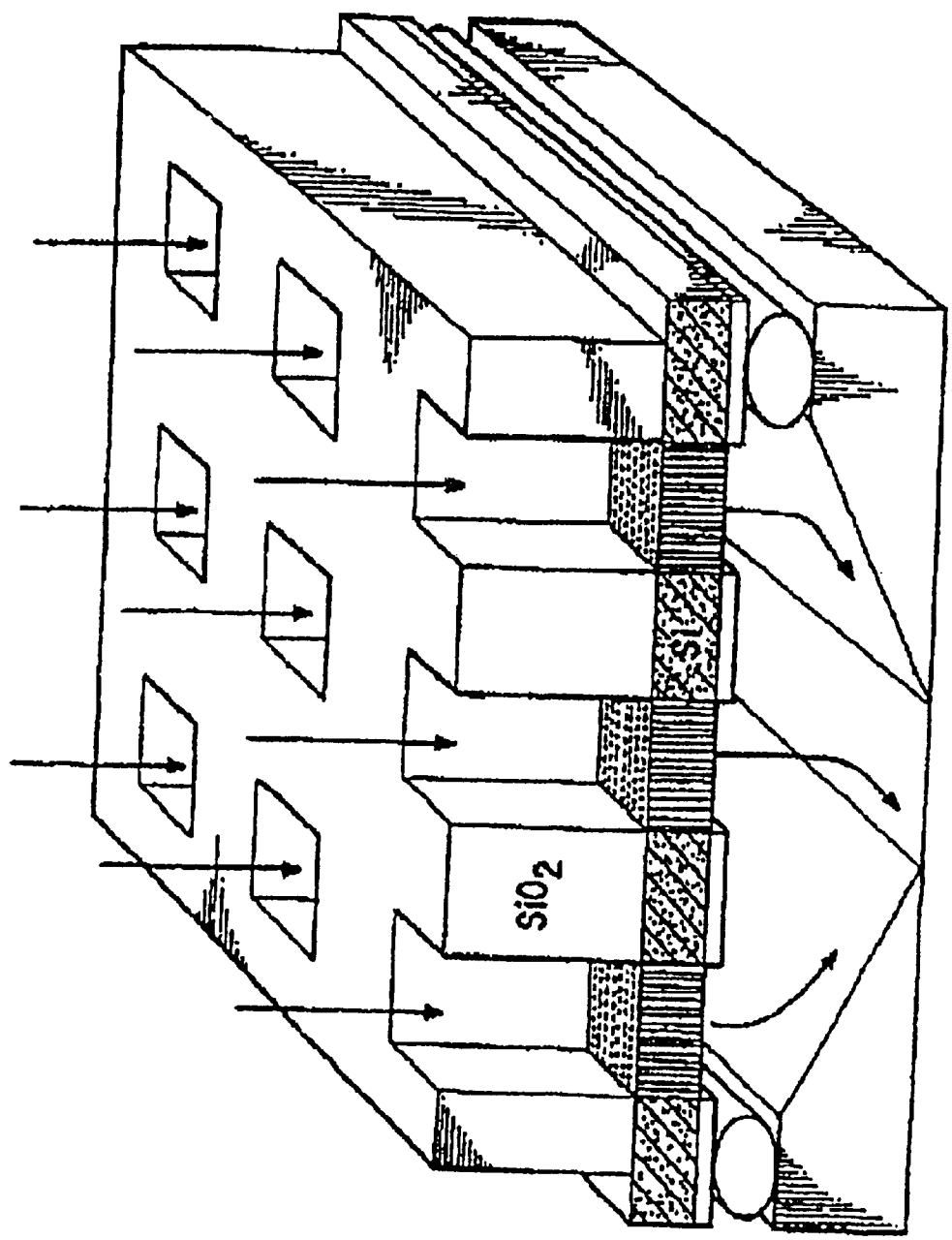
Fig. 8.0

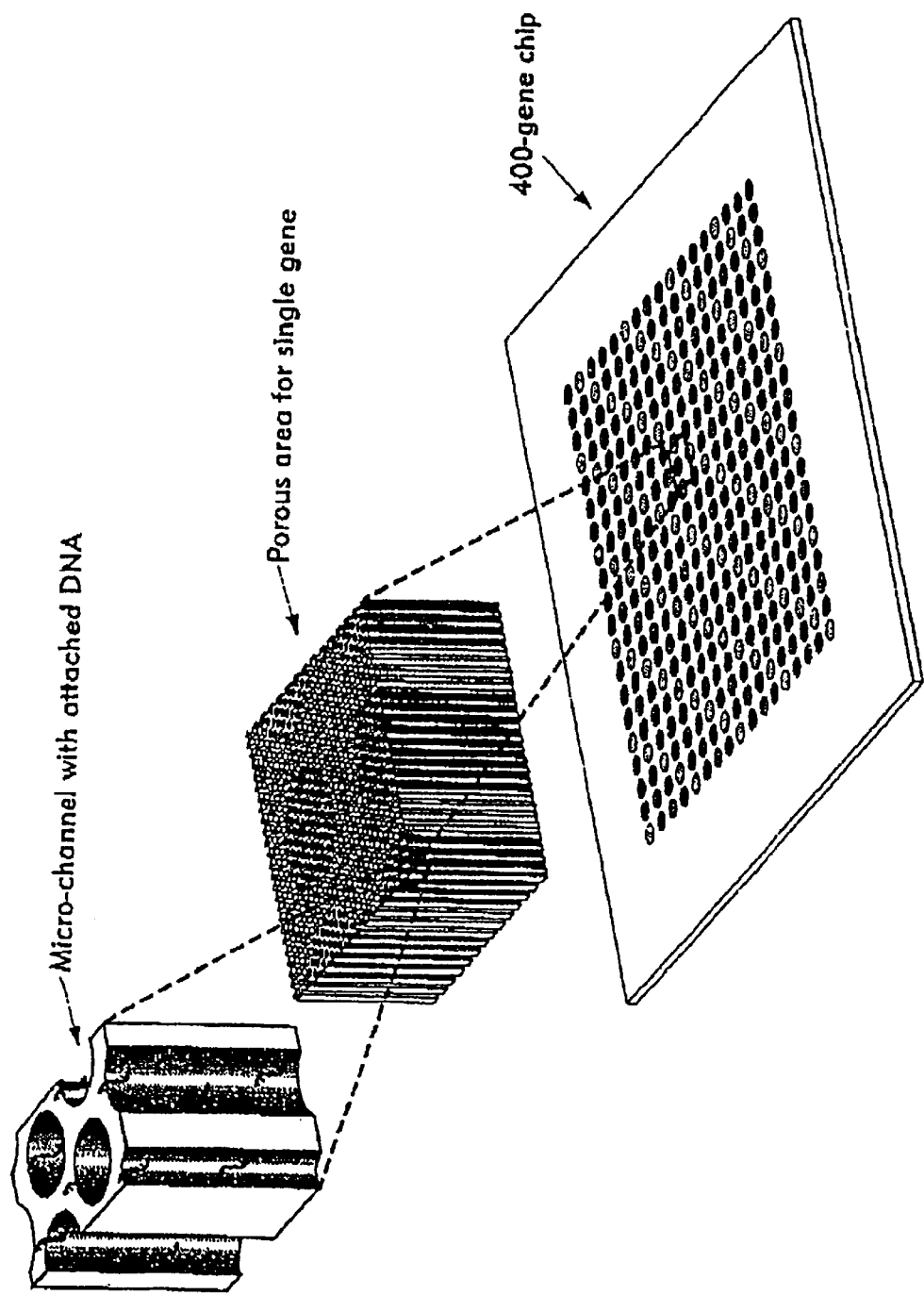
Fig. 9.0

ATTACHMENT CHEMISTRY FOR ORGANIC MOLECULES TO SILICON

This application claims the benefit under 35 U.S.C. 119(e) of U.S. provisional applications Ser. No. 60/111,376, filed Dec. 8, 1998, Ser. No. 60/111,727, filed Dec. 10, 1998, and Ser. No. 60/155,646, filed Sep. 24, 1999, which are incorporated by reference herein in their entirety.

BACKGROUND OF THE INVENTION

The attachment of organic molecules to silicon surfaces is of particular usefulness in a number of technologies and products that involve silicon-based components. For example, organic molecule monolayers may serve as active components in hybrid molecule/silicon electronic devices, as lubrication and anti-stiction coatings in silicon based microelectromechanical systems (MEMS), as masking layer in soft lithography, and as molecular linkages in Si-based chips for gene analysis.

Various methods of Si surface attachment chemistry have been reported, including (i) hydrosilation between alkenes and hydrogen-terminated Si (Linford and Chidsey, U.S. Pat. No. 5,429,708; Linford and Chidsey, *J. Am. Chem. Soc.* 1993, 115; Linford et al., *J. Am. Chem. Soc.* 1995, 117); (ii) the reaction of metal organic reagents with H- or Cl-terminated silicon surfaces (Bansal et al., *J. Am. Chem. Soc.* 1996, 118; He et al. *Chem. Phys. Lett.* 1998, 286; Kim and Laibinis, *J. Am. Chem. Soc.* 1999, 121); (iii) cyclo-addition reactions on clean Si(100) in which the Si=Si surface dimer reacts with C=C or C=C—C=C to form 4- and 6-membered rings, respectively (Hamers et al., U.S. Pat. No. 5,908,692; Hamers et al., *J. Phys. Chem. B* 1997, 101; Teplyakov et al., *J. Am. Chem. Soc.* 1997, 119): and (iv) the electrochemical grafting of hydrocarbon radicals with H-terminated silicon (de Villeneuve et al. *J. Phys. Chem. B* 1997, 101). There have been attempts at grafting organic molecules from the dissociative adsorption of amines on clean Si (Kugler et al., *Surf. Sci.* 1992, 260) and alcohols on H-terminated Si (Cleland, et al., *J. Chem. Soc. Faraday Tran.* 1995, 91; Glass, et al. *Sur Sci.* 1995, 338). In addition, there have been reports on photoinitiated reactions of organic molecules with H-terminated silicon surfaces (Effenberger, et al. *Angew. Chem. Int. Ed.* 1998, 37; Lee et al. *J. Am. Chem. Soc.* 1996, 118).

These assembly processes have various shortcomings. For example, the cyclo-addition reaction can yield well-ordered organic layers but requires clean Si(100) in ultra-high vacuum (UHV) environment. The use of organolithium or Grignard reagent may not be compatible with some semiconductor processes where metal contamination of the surface must be avoided. The high reactivity of these reagents also limits the possibility of functional groups in organic molecules. The hydrosilation process yields dense organic layers but works only in the solution phase and reaction rates are relatively slow. The electrochemical method is limited to a small number of radical species that can be generated in the solution phase. All the above methods are based on the covalent Si—C linkage, which restricts the possibilities of surface chemistry. Other methods based on dissociative adsorption resulted in incomplete organic layers and those using photoactivation were limited to illuminated areas.

Moreover, silicon surface chemistry is of particular interest within the field of biomedical research, wherein the use of Si-based chips for analytical procedures has great benefit in the ability to carry out and/or monitor arrays of assays. Examples include: high-throughput screening for new pharmaceuticals and other chemical entities, toxicology screening, and gene expression screening and analysis, clinical assays, microbiological analysis, environmental testing, food and agricultural analysis, genetic screening, monitoring chemical and biological warfare agents, and process control. Each of these applications involves carrying out and monitoring a reaction where a binding reagent is contacted with a test sample, and the occurrence and extent of binding of the binding reagent with specific components (target moieties) within the test sample is measured in some form. Such chips are described in U.S. Pat. No. 5,843,767 the specification of which are incorporated herein by reference in its entirety.

One widely used analytical procedure in genome mapping illustrative of such applications is hybridization of membrane-immobilized DNAs with labeled DNA probes. Robotic devices currently enable gridding of 10,000–15,000 different target DNAs onto a 12 cm×8 cm membrane. See for example, Drmanac et al. in Adams et al. (Eds.), Automated DNA Sequencing and Analysis, Academic Press, London, 1994 and Meier-Ewert et al. Science 361:375–376 (1993). Hybridization of DNA probes to such membranes has numerous applications in genome mapping, including generation of linearly ordered libraries, mapping of cloned genomic segments to specific chromosomes or mega YACs, cross connection of cloned sequences in cDNA and genomic libraries, and so forth.

Genosensors, or miniaturized "DNA chips" currently are being developed for detection of multiple binding reactions such as hybridization analysis of DNA samples. DNA chips typically employ arrays of DNA probes tethered to flat surfaces to acquire a hybridization pattern reflecting the nucleotide sequence of the target DNA. See, for example, Fodor et al. Science, 251:767–773 (1991); Southern et al. Genomics 13:1008–1017 (1992); Eggers et al. Advances in DNA Sequencing Technology, SPIE Conference, Los Angeles, Calif. (1993); and Beattie et al. Clin. Chem. 39:719–722 (1993). Such devices may be applied in carrying out and monitoring other binding reactions, such as antibody capture and receptor binding reactions.

However, miniaturization of DNA hybridization arrays or other types of binding arrays on silicon surfaces or other two-dimensional surfaces comprising silicon has been limited by the paucity of methodologies for attaching organic targeting molecules to the silicon surface.

It is apparent, therefore that more convenient and general methods for attaching organic molecules to silicon surfaces are desirable. Methods that are more efficient, and impart fewer limitations on surface chemistry are particularly desirable.

SUMMARY OF THE INVENTION

It is therefore an object of the present invention to provide methods that greatly increase the efficiency for the attachment of organic molecules on silicon.

In accomplishing the foregoing object of the invention, there has been provided, in accordance with one aspect of the invention, a method for attaching organic molecules to a silicon surface comprising reacting an organic molecule containing nucleophilic functionality with a halogenated silicon surface.

In an embodiment of the invention, the method of the present invention can be performed in solution phase or in a substantially vacuum environment via a gas-surface reaction.

In another embodiment of the invention, there is provided a method for preparing a halogenated silicon surface by reacting a silicon surface with a halogen source to form a halogenated silicon surface.

There is also provided, in yet another aspect of the invention, a surface material comprising an organic molecule covalently bonded to a silicon surface, wherein said surface material is produced by a process comprising reacting a nucleophilic organic molecule with a halogenated silicon surface.

In yet another aspect of the invention there is provided a method of producing an improved device for detecting multiple binding reactions comprising reacting an organic molecule containing a nucleophilic functionality with a halogenated silicon surface of said device. In a preferred embodiment, the organic molecule is a binding reagent effective for sequence analysis by hybridization, analysis of patterns of gene expression by hybridization of mRNA or cDNA to gene-specific probes, immunochemical analysis of protein mixtures, epitope mapping, assay of receptor-ligand interactions and profiling of cellular populations involving binding of cell surface molecules to specific ligands or receptors. In another embodiment, the organic molecule is capable of linking to a binding reagent In further embodiments, the binding reagents are selected from the group consisting of DNA, proteins and ligands, and in a particular embodiment are oligonucleotide probes.

In yet another preferred embodiment, the binding reagents are attached within densely packed channels of a solid substrate.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3A shows a set of XP spectra taken after the Si(100)–(2×1):Cl surface has been exposed to increasing amounts (0–135 torrs) of butylamine at 400 K.

FIG. 3B shows relative XPS intensities as a function of butylamine exposure to Si(100)–(2×1):Cl and fits (curves) based on Langmuir kinetics and a single rate constant. Solid circles: $C_{1s}/Si_{2p}$ ; solid squares: $N_{1s}/Si_{2p}$; triangles: $Cl_{2p}/Si_{2p}$.

FIG. 6 shows annealing series of $C_{1s}$ for octylamine and aniline assembled on Si(100).

FIG. 8 depicts a porous silicon wafer with integral sample wells.

FIG. 9 shows a DNA flow-through chip.

DETAILED DESCRIPTION

The present invention provides convenient methods of attaching an organic molecule to a silicon surface, in particular, the methods of the invention provide attachment of organic nucleophilic compounds to silicon surfaces. The attachment is achieved by reacting an organic nucleophile with a halogenated silicon surface.

It will be generally understood that the methods of the present invention contemplate silicon substrates in which the silicon is available for reaction with halogen and organic nucleophilic compounds. This includes, for example, doped or non doped silicon, silicon of diverse crystalline orientations, single crystal or polycrystal silicon, porous silicon, flat silicon and amorphous silicon.

Figure 1:
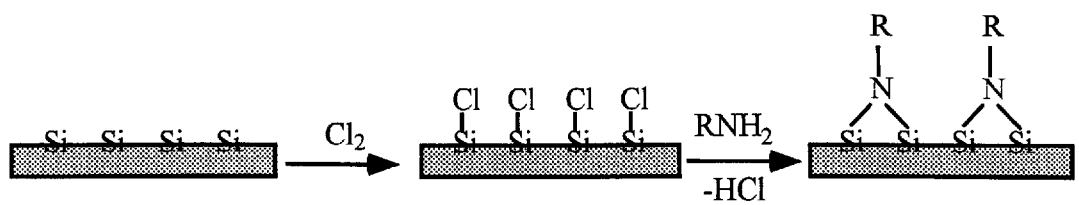
FIG. 1 shows a two step process for the formation of monolayer assembly on silicon surface via $Si_2$=N linkages. R represents an organic functional group.
Figure 2:
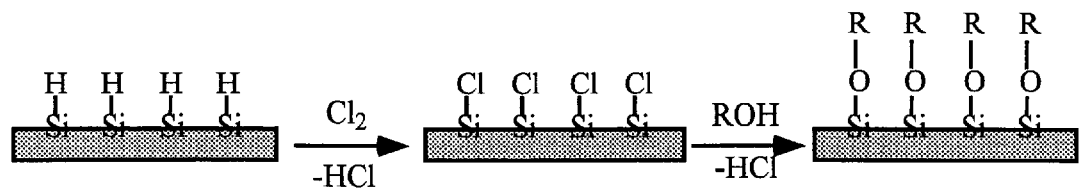
FIG. 2 shows a two step process for the formation of monolayer assembly on silicon surface via Si—O linkages. R represents an organic functional group.

The methods of the present invention are applicable to silicon surfaces in general and the reaction of the present invention is sufficient for the attachment and assembly of organic molecules with nucleophilic functionalities on halogenated silicon surfaces, as shown generally, for example, in FIGS. 1 and 2 where $RNH_2$ and ROH are organic compounds containing the nucleophilic functionality of —$NH_2$ or —OH, respectively. Organic compounds containing other nucleophilic functionalities, such as =NH, —SH, —SeH, —TeH, and —$PH_2$ are also applicable for attachment.

The halogenated surface silicon of the present invention is provided by one of the two methods. In the first method, the halogenated surface silicon is obtained from the reaction of clean silicon surface with a halogen source in a substantially vacuum environment. Prior to reaction with the halogen source, a clean Si surface may be prepared by heating the surface in vacuo to a temperature sufficient to substantially clean the silicon surface of impurities. Other methods of preparing clean silicon surfaces are known in the art, and are suitable for use in the invention. For example, plasma cleaning and reactive ion etching also may be used to prepare the clean surface. Saturation doses of halogen typically are used to form monohalogenated silicon surfaces.

In the second method, the halogenated surface silicon is obtained from the reaction of hydrogen terminated silicon surfaces with a halogen source in a substantially vacuum environment. In general, halogenation reactions may be carried out at ambient temperatures and reduced pressures. However, elevated reaction temperatures and ambient pressures may be used.

Alternatively, the second method of the present invention may be advantageously practiced in solution phase. The reaction proceeds through a radical intermediate and catalytic amounts of radical initiators may be added to promote the reaction. Radical initiators such as azocompounds, peroxides, photons, and tin-containing radical initiators such as $Bu_3SnH$. Preferably, benzoyl peroxide is used as a radical initiator. In a preferred embodiment, the halogenation reaction is chlorination, which may be carried out with, for example, $Cl_2$, $SO_2Cl_2$, $Cl_3CSO_2Cl$, n-chlorosuccinimide, $C_6H_5Cl_2$ and $PCl_5$. The skilled artisan will appreciate however that other chlorine sources also may be used.

Nucleophilic substitution reactions of the present invention conveniently include both substantially vacuum and solution phase environments. Generally, the reaction in vacuum comprises gas-surface exposure of the halogenated surface to organic nucleophiles. A typical reaction time of about 2 hrs. displaces over 90 to 95% of surface chlorine with amine molecules. However, it will be understood that the degree of attachment of organic nucleophiles per area of surface and the total quantities of organic nucleophiles attached may be tailored to the desired level. Methods of achieving this variation are within the scope of the present invention. To decrease risk of surface contamination, the organic nucleophiles may be purified, for example, by distillation.

For solution phase reaction, the chlorinated silicon sample is generally reacted with the desired organic nucleophile for about 24 hrs, to provide silicon surfaces with attached organic molecules. The conditions of the nucleophile attachment reaction are not critical to the methods of the present invention and can practically be between substantially ambient to elevated temperatures and/or pressures and with dilute solutions to neat nucleophile as desired or needed.

The nucleophilic organic compounds to be attached to the silicon surfaces of the present invention include those organic compounds which contain a nucleophilic functionality that will react with halogenated silicon surfaces as described herein. The methods of the present invention are of particular advantage when the nucleophilic organic compound contains a $—NH_2$, $—NH$, $—OH$, $—SH$ or $—PH_2$ nucleophile. The skilled artisan will be aware that the desired organic compound for attachment can include other nucleophilic functionalities known in the art and use of such are within the scope of the present invention.

The methods of the present invention are particularly applicable in the preparation of Si-based devices for the detection of multiple binding reactions. Particularly, the methods of the present invention can provide organic molecules attached to silicon surfaces of devices for carrying out and detecting binding reactions, in which the organic molecules are binding reagents (or "probes").

It is contemplated that a bifunctional molecule is reacted with the silicon surface which provides a point of attachment for a biological probe such as an oligonucleotide or peptide. The bifunctional molecule comprises at least two functional groups of differing reactivity for silicon surface binding and attaching biological probes. The functional groups have different reactivities toward chlorinated silicon to prevent both functional groups binding to the surface. For example, —OH groups will react with a halogen on the silicon surface while —SH or —NH2 groups can be linked to biological molecules. A spacer portion of the molecule serves to separate the functional groups into a surface-binding region and a probe-attachment region.

The spacer portion preferably is long enough to act as an insulator against quenching of a detectable label by silicon. Generally, a spacer comprising a chain of 6 to 25 atoms will provide adequate insulating and detection properties. Thus, a chain containing 6 to 25 methylene groups is suitable. In another embodiment, the chain may contain a poly (ethyleneglycol) chain containing 2 to 50 —(CH2CH2)—O— monomers. Other spacer units are known in the art and may be used. By varying the length of the spacer it is possible to change the insulating properties of the monolayer film deposited on a silicon surface. Such an ability to fine-tune insulating properties via the monolayer in this manner is valuable for a number of applications. For example, fine control in the overlap of electronic states is afforded by a thin layer, whereas for standard fluorescence measurements a thick layer is desirable to prevent quenching by the surface. In particular, these options with respect to the surface layer are provided by virtue of the close-packed hydrocarbon layer that can be formed at the Si—Cl surface.

The biological molecule may be attached directly to the spacer, or may be linked via another bifunctional spacer. For example, a free amine group may be directly linked to a biological molecule containing an active ester moiety, such as an N-hydroxysuccinimide ester, or a water soluble derivative thereof, such as an N-hydroxysuccinimide ester containing a sulfate group in the succinimide ring. In another embodiment, a free sulfhydryl group can be linked to a biological molecule that contains a maleimido or vinyl pyridine group. Other methods of linkage of biological molecules via selective reaction with amine and sulfhydryl groups are well known in the art. Alternatively, the spacer may be attached to the biological molecule via another bifunctional linker. Suitable bifunctional linkers are well known in the art and are commercially available, for example from Pierce Chemical Co. (Rockford, Ill.). Examples include linkers containing a maleimido function and an n-hydroxysuccinimide ester, and water soluble derivatives. The skilled artisan will recognize that the present invention is not limited to particular bifunctional spacer molecules and combinations of spacer molecules, and may be practised using a wide variety of spacer chemistries that presently are known or that are discovered in the future.

In a particular embodiment, the binding reagents are attached within channels densely packed in a solid substrate. The solid substrate contains a first and a second surface, where the channels extend through the substrate from the first to the second surface. The first and second surfaces of the substrate may be planar, and also may be parallel, although non-planar and non-parallel surfaces may be used. Suitable substrate materials include porous silicon, which may be produced using known microfabrication techniques.

Binding to reagents in the flow-through devices can be detected by devices and methods that are well known in the art including, but not limited to, microfabricated optical and electronic detection components, film, charge-coupled-device arrays, camera systems and phosphor storage technology.

The surfaces of the devices prepared by means of the present invention contribute to overcoming limitations inherent in current solid phase methods for detecting binding reactions by eliminating the diffusion-limited step in flat surface binding reactions, and by increasing the amount of binding reagent present per unit area of the two-dimensional surface on the face of the substrate. In a particular illustrative embodiment in this regard, the device may be used as a "genosensor," where the binding reagent is an oligonucleotide or polynucleic acid that is immobilized in the channels of the substrate, and in which the analyte is a nucleic acid that is detected by hybridization (base pairing) to the binding reagent.

The methods of the present invention produce such devices used to characterize or otherwise identify molecular species that bind to a particular binding reagent via essentially any mode of specific molecular binding, including known modes of binding and modes that will be discovered in the future. For example, the novel devices may be used to detect: antibody-antigen and ligand-receptor binding; nucleic acid hybridization reactions, including DNA-DNA, DNA-RNA, and RNA-RNA binding; nucleic acid-protein binding, for example in binding of transcription factors and other DNA-binding proteins; and binding reactions involving intact cells or cellular organelles. In one particular embodiment, the device may be used for DNA sequence analysis.

The present invention, thus generally described, will be understood more readily by reference to the following examples, which are provided by way of illustration and are not intended to be limiting of the present invention.

A. Attachment on Clean Si (100)

Attachment reactions were carried out on clean Si(100) in vacuum. The clean Si(100)–(2×1) surface was prepared by heating a native oxide covered surface in vacuum environment to above 1250 K. The resulting surface was exposed to a saturation dose of $Cl_2$ in vacuum at 300 K to form the monochloride Si(100)–(2×1)Cl surface, which was subsequently transferred to a high vacuum reactor attached to the ultra-high vacuum (UHV) chamber and exposed to amine molecules at a gas pressure of $1\times10^{-2}$ torr and a surface temperature of 450 K for about 2 hours. The sample was transferred back to UHV for surface analysis by X-ray photoelectron spectroscopy (XPS) or to the ambient for external analysis.

The growth of organic monolayers on the Si(100) surface is followed by XPS. The Mg Kα X-ray (1253.6 eV) was from an anode source (VG) operated at 200 Watts. Photoelectrons were detected by a hemispherical analyzer (VG100) using a pass energy (PE) of 100 eV. The binding energy scale was referenced to the substrate $Si_{2p}$ peak (not shown) at BE=99.3 eV. FIG. 3A shows a set of XP spectra taken after the Si(100)–(2×1):Cl surface has been exposed to (from bottom to top) increasing amounts of n-butylamine ($C_4H_9NH_2$) at a surface temperature of 450 K. The growth of the organic monolayer is evidenced by the decrease in $Cl_{2p}$ and the increase in $N_{1s}$ and $C^{1s}$ intensities with $C_4H_9NH_2$ exposure. The peak intensities (normalized to that of $Si_{2p}$) are summarized in FIG. 3B (open triangles: $Cl_{2p}/Si_{2p}$; solid circles: $C_{1s}/Si_{2p}$; solid squares: $N_{1s}/Si_{2p}$). These normalized peak intensities are proportional to surface coverages. The lines are fits to simple Langmuir kinetics based on the following equations:

$$\theta_{Cl} = 1.0 \cdot e^{-k \cdot p \cdot t}$$

$$\theta_m = 0.5 \cdot (1 - e^{-k \cdot p \cdot t}) \quad (1),$$

where k is the rate constant; p is the amine pressure; t is reaction time; $\theta_{Cl}$ and $\theta_m$ (in monolayers) are surface coverages of Cl and assembled molecules, respectively. We have assumed that the starting Cl coverage is one monolayer (ML) and the saturation molecular coverage is 0.5 ML. The fits yield a rate constant of $0.031\pm0.005$ torr$^{-1}$s$^{-1}$. Based on this rate constant, the reaction is 90% complete for a total exposure time of two hours at an amine pressure of $1\times10^{-2}$ torr.

Figure 4:
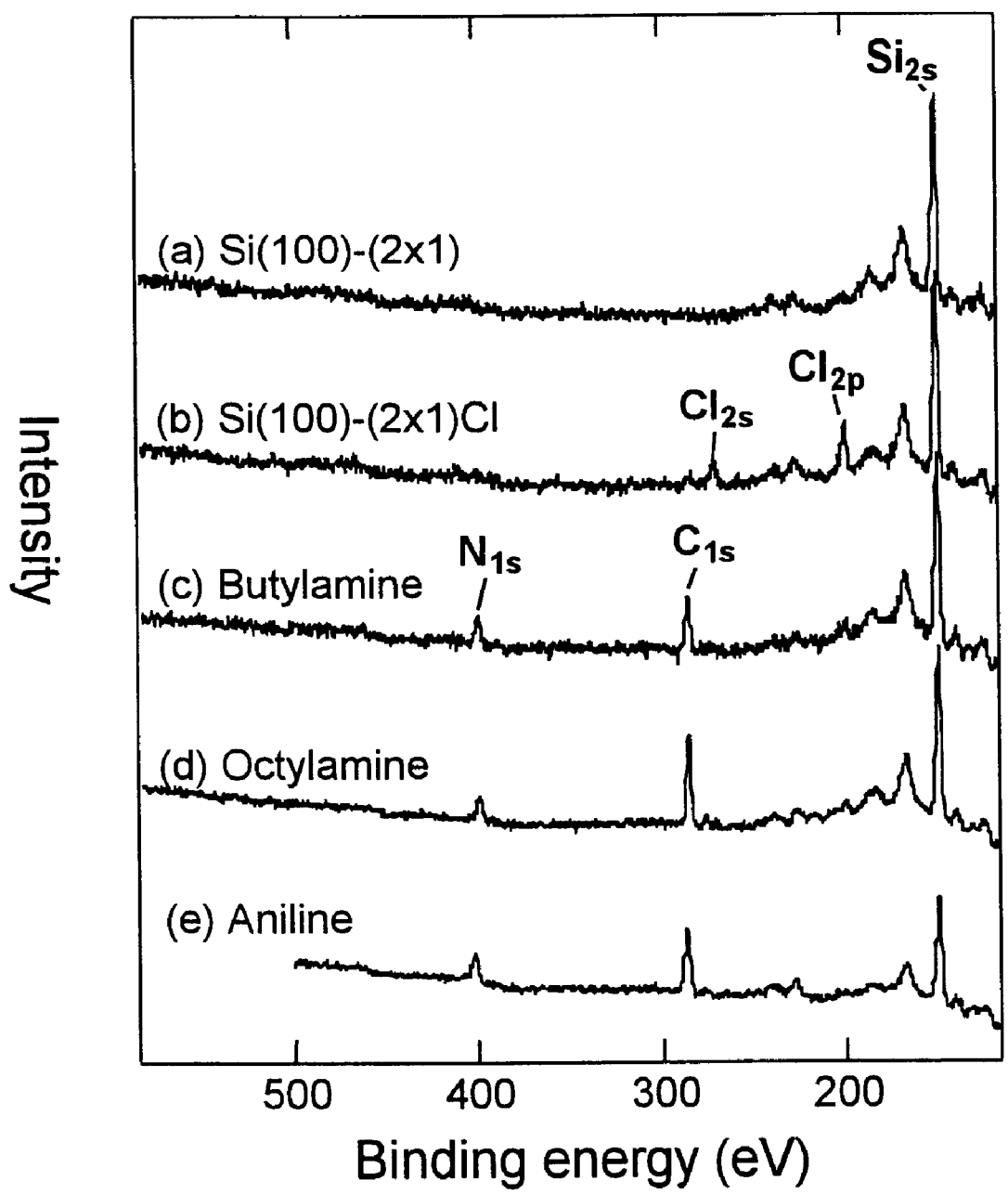
FIG. 4 shows a set of XP spectra for (a) clean Si(100)–(2×1); (b) Si(100)–(2×1)Cl; and the surface after attachment reactions with (c) butylamine, (d) octylamine, and (e) aniline.

FIG. 4 shows X-ray photoelectron spectra (XPS) for (a) clean Si(100)–(2×1); (b) Si(100)–(2×1)Cl; (c) $C_4H_9N/Si$(100); (d) $C_8H_{17}N/Si$(100); (e) $C_6H_5N/Si$(100). The main peaks are labeled on each spectrum. The weak features at ~230 eV are from a small Ta clip used to attach a thermal couple to the Si sample. Both the clean and the monochloride covered Si(100) surfaces show only trace amounts of carbon. After reaction with RNH2 for two hours, the Cl peaks become negligible while the $C_{1s}$ and $N_{1s}$ peaks appear. This result points to the near completion of the attachment reaction.

Figure 5:
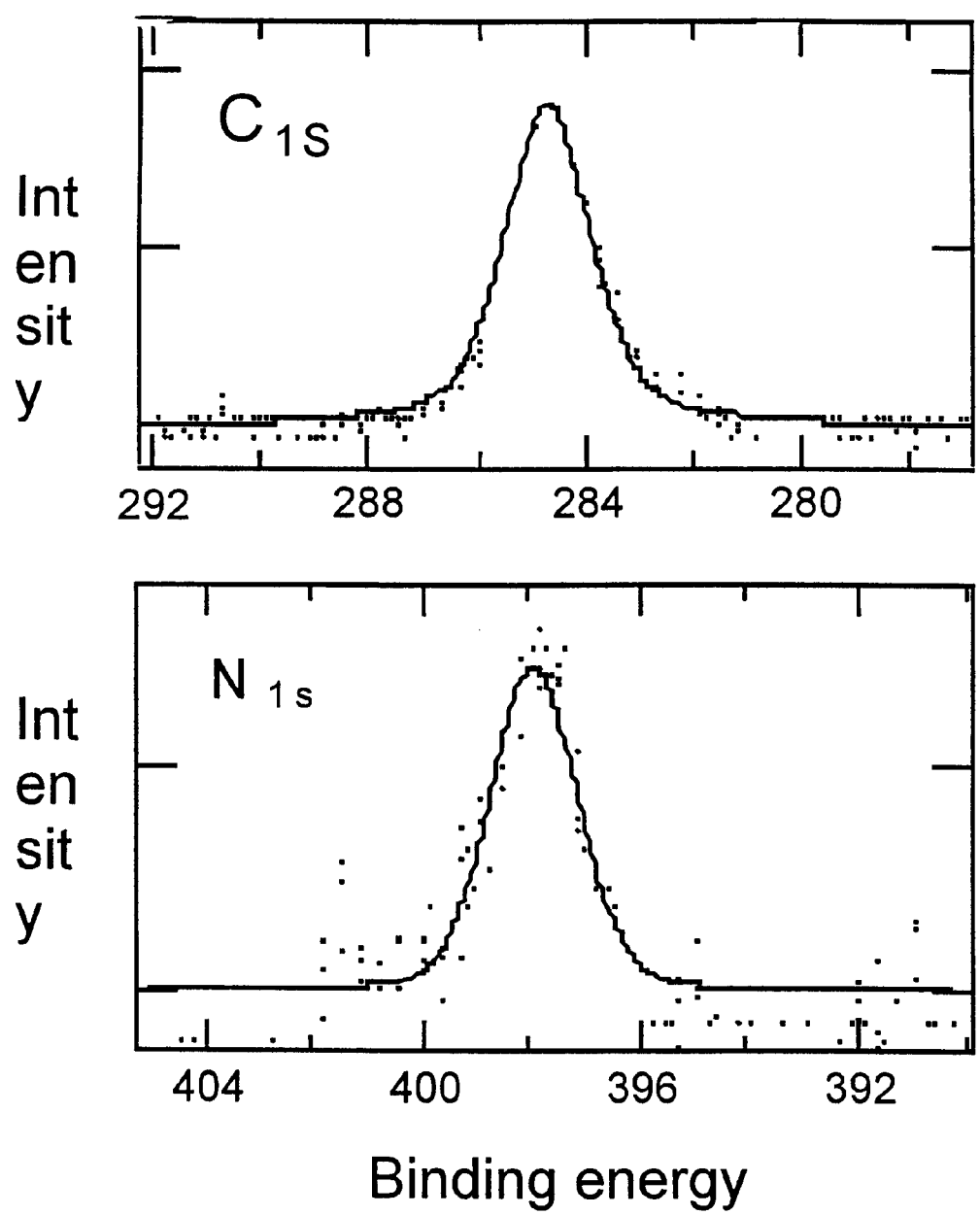
FIG. 5 shows high resolution XPS scans of the $C_{1s}$ and $N_{1s}$ regions in the octylamine assembly on Si(100).

Each organic molecule in the above assembly process is attached to Si(100) via the —$NSi_2$ anchor. Evidence for this comes from $C_{1s}$ and $N_{1s}$ binding energies, as shown in high resolution scans in FIG. 5 for octylamine assembled surface. Similar results are obtained for butylamine and aniline assembled surfaces. The $C_{1s}$ binding energy (BE) of the assembled molecule is BE=$284.7\pm0.1$ eV, as expected for saturated alkyls. The binding energies of the $N_{1s}$ peak is BE=397.9–398.0 eV. The observed $N_{1s}$ binding energy is higher than that for bulk silicon nitride (397.4 eV), but significantly lower than the typical value of ~399–399.5 eV for amine molecules. In an experimental and theoretical study of the dissociative adsorption of aniline and 1,4-phenylenediamine on Si(100), Kugler et al. found that the $N_{1s}$ binding energy of bridge bonded species, —$C_6H_4$—$NSi_2$, is 397.9 eV while that for singly bonded—$C_6H_4$—NHSi is 398.6 eV [Kugler, et al., Surf. Sci. 1992, 260]. The surface species resulting from the present method using amines can be assigned to R—$NSi_2$, i.e., the N atom is bridge-bonded to two surface silicon atoms.

Based on stoichiometry, the resulting organic layer corresponds to a surface coverage of 0.5 ML (molecule to surface Si atom ratio) with each molecule attached to the surface possibly via bonding to two silicon atoms, as illustrated in reaction 1. This coverage also is consistent with XPS analysis, showing the depletion of substrate Si photoelectron intensity upon molecular layer formation.

Table 1, below, compares experimental intensity ratios with predictions using a simple atomic layer model in which each overlayer attenuates photoelectron intensity escaping from the underlying layer based on the following equation:

$$I_i = I_{i-1}(1-\theta) + I_{i-1} \cdot \theta \cdot \exp\left(-\frac{d_i}{\lambda \cos\alpha}\right)$$

where $I_i$ and $I_{i-1}$ are the substrate photoelectron intensities escaping from the ith and (i–1)th atomic overlayer, respectively. $I_0$ is the intensity from the clean surface; is the coverage of the atomic layer. θ is 0.5 for all atomic layers in the alkylamine assemblies, and for the 1st (N), 2nd (C), & 5th (C) atomic layers in the aniline assembly. θ is 1.0 for the 3rd (C) and 4th (C) layers in the aniline assembly. The overlayer thickness, $d_i$, is simply chosen as the atomic diameter (1.4 & 1.3 Å for C and N, respectively). A universal mean free path of λ=18 Å is used for the $Si_{2p}$ photoelectron. The angle of detection is α=50° (from surface normal). Considering the simplicity of the model and the estimated experimental error range of ±10%, the agreement between measurement and calculation is satisfactory.

TABLE 1

Ratios of $Si_{2p}$ XPS intensity between each surface assembly and clean Si(100)

| $I/I_0$ ($Si_{2p}$) | $C_4H_9N/Si(100)$ | $C_8H_{17}N/Si(100)$ | $C_6H_5N/Si(100)$ |
|---|---|---|---|
| Experimental | 0.69 ± 0.07 | 0.67 ± 0.07 | 0.60 ± 0.06 |
| Calculated | 0.75 | 0.59 | 0.66 |

The thermal stability of the surface assembly is studied in UHV by recording XP spectra after annealing the surface at various temperatures. For $N_{1s}$, both peak position and intensity change only slightly upon heating. More significant change is seen in the $C_{1s}$ region. FIG. 6 shows annealing series of $C_{1s}$ for octylamine and aniline assembled on Si(100). In FIG. 6, Panel (a): C1s region of the XP spectra for octylamine assembled surface, $C_8H_{17}N/Si(100)$, taken after the surface has been annealed at the indicated temperatures; Panel (b): C1s region of the XP spectra for aniline assembled surface, $C_6H_5N/Si(100)$, taken after the surface has been annealed at the indicated temperatures; Panel (c): $C_{1s}/Si_{2p}$XPS peak intensity ratio as a function of annealing temperature for $C_8H_7N/Si(100)$; Panel (d): $C_{1s}/Si_{2p}$ intensity ratio as a function of annealing temperature for $C_6H_5N/Si(100)$. For the octylamine assembly (panel a), while the position of $C_{1s}$ remains constant between 450 and 600 K, there is a small decrease in peak intensity. More significant decrease in intensity is seen above 600 K. The remaining alkyl chain decomposes on the surface above 750 K, as evidenced by the shift in BE toward 283 eV, typical for carbides, with increasing temperature. The dependence of $C_{1s}/Si_{2p}$ratio for octylamine as a function of annealing temperature is summarized in panel c. There is a continuous drop in $C_{1s}/Si_{2p}$with increasing temperature, particularly above 600 K, indicating a loss (desorption) of carbon containing species from the surface upon heating. A similar thermal behavior is observed for butylamine.

The aniline assembled surface is thermally more stable than the alkyl layer, panel b of FIG. 6. The XP spectra remain identical from 450 to 750 K, indicating no chemical change in this temperature window. A decrease in peak intensity and a shift in peak position is seen only at temperatures above 750 K. The temperature dependence of the $C_{1s}/Si_{2p}$ratio is shown in panel d. This ratio decreases by no more than 10% when the surface temperature is increased from 450 to 750 K. Significant decrease in $C_{1s}/Si_{2p}$ratio is only seen above 750 K. Note that the $C_{1s}/Si_{2p}$ ratio at 450 K for the aniline assembly is slightly higher than that for the octylamine assembly, although the total number of carbon atoms per molecule in the former is smaller. This is because the $C_{1s}$ signal is less attenuated in the aniline assembly than in the octylamine layer.

The rectangular unit cell of the Si(100)–(2×1) surface is 7.68 Å×3.84 Å. Assuming one assembled molecule for each surface dimer, the surface density is one molecule per 29.5 Å$^2$. This packing density is lower than that of one molecule per 21.6 Å in the well known alkanethiol monolayer on Au(111). The reason that the aniline assembly is more stable than the alkyl attachment may be attributed in part to differences in surface packing and ordering. The Van der Waals size of an assembled phenyl ring is 6.7 Å×3.4 Å (width×thickness). This is ~90% of the size of the unit cell on the Si(100)–(2×1) surface.

B. Attachment on Porous Si

An amination reaction also was carried out on porous silicon using surfaces prepared both in the gas phase and in solution. The porous silicon samples were prepared using the standard anodization procedure. For the gas-solid assembly reaction, the hydrogen terminated porous silicon sample is transferred to the UHV chamber. After heating to >900 K in UHV to desorb surface hydrogen, the sample is subject to the two step chlorination and butylamine assembly reaction under conditions identical to those for the Si(100) surface outlined above. The sample is then removed from UHV and characterized by transmission Fourier-Transform Infrared (FTIR) spectroscopy under ambient conditions.

Figure 10:
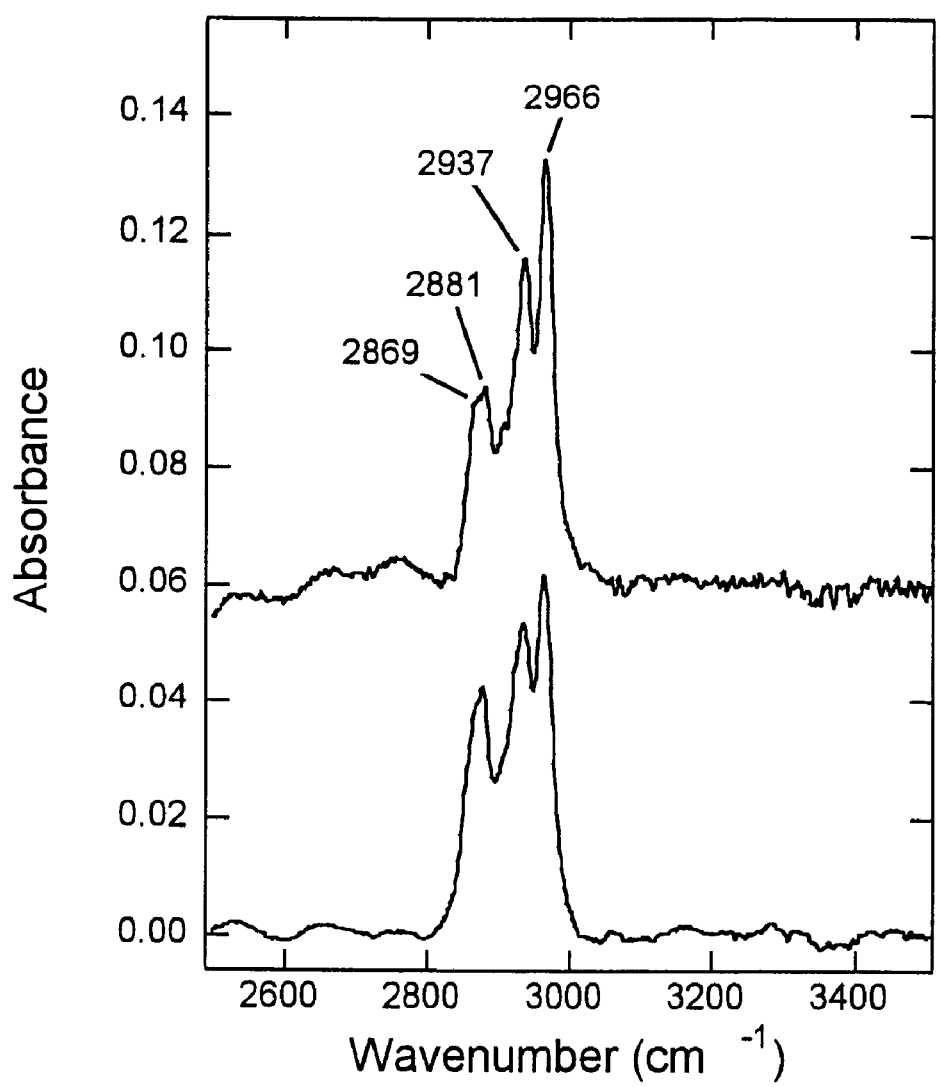
FIG. 10 compares the FTIR spectra of butylamine assembled on porous silicon using the gas-surface (upper) and the solution phase (lower) assembly methods.

For solution phase assembly, the hydrogen terminated porous silicon sample was chlorinated in deoxygenated chlorobenzene at 100° C. for 1 hour by using $PCl_5$ as a chlorine source and a catalytic amount of benzoyl peroxide as a radical initiator. Chlorination was carried out in a sealed reaction vessel under a blanket of anhydrous argon. The chlorinated silicon sample was then immersed in deoxygenated butylamine (transferred to the silicon chips via a cannula) at 80° C. for 24 hours. At the end of the reaction, the sample was thoroughly rinsed with $CH_2Cl_2$ and dried on a vacuum pump (1 mmHg) before being characterized by transmission FTIR. FIG. 10 shows transmission FTIR spectra for butylamine assembled on chlorinated porous silicon surface. The surfaces were obtained from gas-surface reactions (upper) and solution phase reactions (lower). The intensities of the two spectra have been normalized. The main peaks are: 2966 and 2937 cm$^{-1}$ for asymmetric C—H stretches in —$CH_3$ and —$CH_2$—, respectively and 2869 and 2881 cm$^{-1}$ for symmetric C—H stretches in —$CH_3$ and $CH_2$—. Both give C—H stretch peaks (2869, 2881, 2937, 2966 cm$^{-1}$) characteristic of the butyl group. The absence of the N-H stretch peak (~3300 cm$^{-1}$) provides strong support for the proposed reaction mechanism in which the N atom is bridged between two surface silicon atoms. Also seen consistently in these FTIR spectra are peaks at 1460 cm$^{-1}$ and 1220 cm$^{-1}$ (not shown in FIG. 10). While the 1460 cm$^{-1}$ peak is the $CH_2$—$CH_3$ stretching frequency, the 1220 cm$_{-1}$ peak is characteristic of a tertiary C—N stretching frequency. This further supports the notion that the N atom likely is bonded to two Si atoms on the surface. It has been found that an important step in the solution phase reaction is chlorination, which is mainly responsible for the final coverage of the surface assembly. FTIR taken after long time air-exposure did not show significant change, pointing to the chemical stability of the organic layer.

C. Monolayers on Silicon Surfaces via Si—O Linkages

Assembly reactions were performed on Si(100) and Si(111) wafers or parallelogram plates (ATR-plates) designed for multiple internal reflection spectroscopy. The silicon samples were cleaned by rinsing with $CH_2Cl_2$, dried, and then oxidized in 3:1 concentrated $H_2SO_4$:30% $H_2O_2$ for 2 hours at 100° C., followed by thorough rinsing with 18MΩ·cm $H_2O$. The surface was etched in nitrogen-sparged 40 % aqueous $NH_3F$ solution for 4 minutes to create a monohydride silicon surface with low defect density. The silicon surface was then rinsed with 18MΩ·cm $H_2O$ for 30 seconds each side, then with MeOH and dried under argon. Upon drying, the crystals were transferred to a glass reaction cell which was connected to a stainless steel vacuum line via an adapter. The cell was evacuated to a base pressure of 1×10$^{-5}$ torr. The sample was then exposed to 0.2 torr of $Cl_2$ gas while under illumination by a 300 W tungsten lamp for 2 minutes on each side to form the Si-Cl surface. The residual chlorine was evacuated and the reaction cell was back-filled with dry argon.

Two alcohol molecules, dodecanol (C12) and octadocanol (C18), were used in the experiment. Solution (0.1–0.001 M) of each alcohol dissolved in iso-octane was transferred to the reaction cell using a metal cannula. Each surface was immersed in the solution for 14 hours at 40° C. under argon. Following each reaction, the Si sample was rinsed with several portions of MeOH and $CH_2Cl_2$. Optionally, the sample was also sonicated in $CH_2Cl_2$ for 5 minutes.

Note: All reagents were purchased from Aldrich Chemical Company (Milwaukee, Wis.). $CH_2Cl_2$ and MeOH were HPLC grade. Dodecanol was distilled from $CaH_2$ and stored over molecular sieves. Octadecanol was used as received. Iso-octane was distilled before use.

FTIR spectra were taken on a modified MIDAC M2510-C spectrometer with a liquid nitrogen cooled mercury-cadmium-telluride detector. The complete system was purged with purified nitrogen gas. All spectra were taken with an instrument resolution of 4 cm$^{-1}$. A freshly oxidized Si ATR sample was used as background. Contact angle measurements were taken with 5 µL drops of water using a goniomezer. AFM imaging of the surface was carried out with the NanoScope IIIa from Digital Instruments. An oxide sharpened silicon nitride rip with a nominal force constant of 0.06 N/m and a nominal tip radius of ~30 nm was employed. Images were taken in the contact mode at 30 Hz scan frequency and zero applied load.

Figure 11:
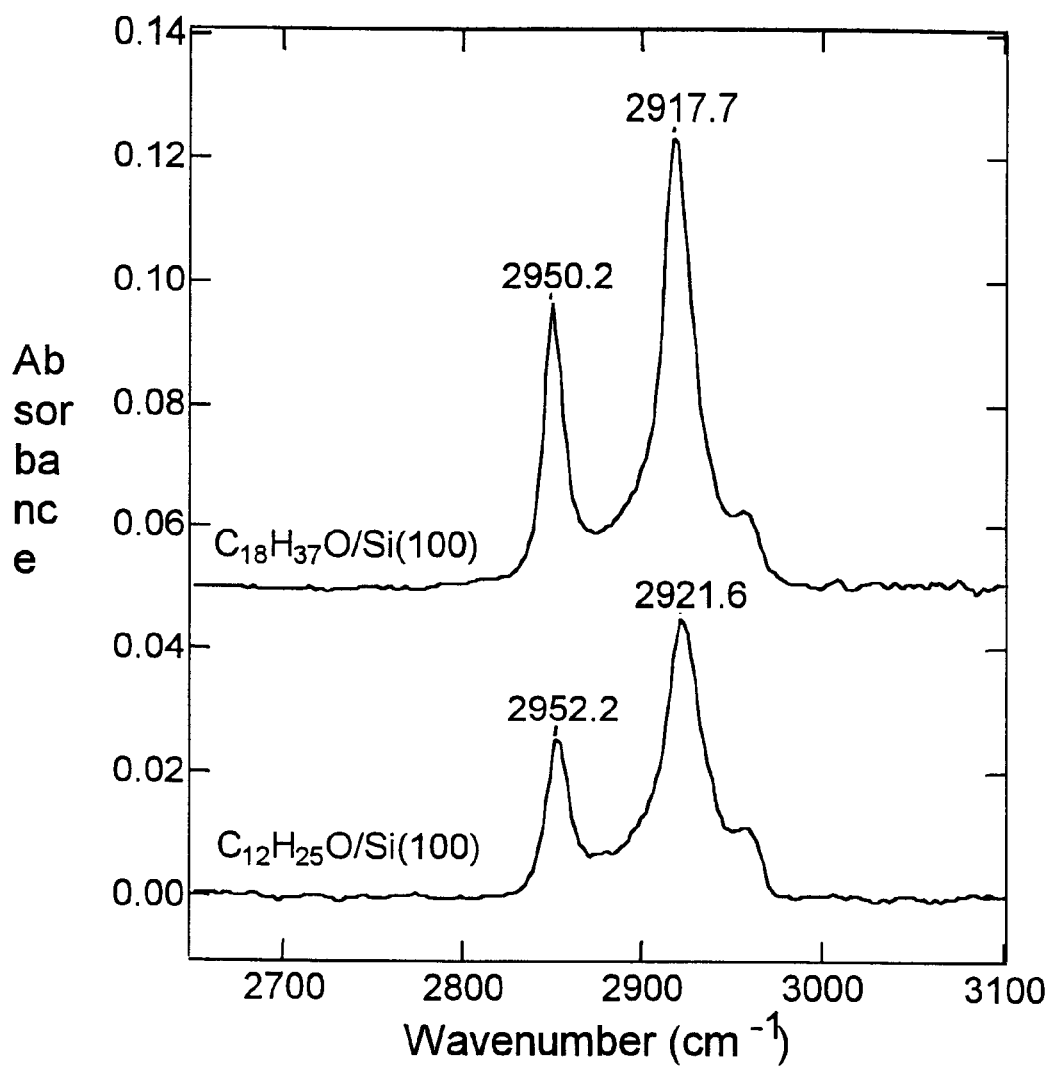
FIG. 11 shows FTIR spectra of dodecanol and octadecanol assemblies on Si(100) surfaces.

FIG. 11 shows FTIR spectra of dodecanol (lower) and octadecanol (upper) assembly on Si(100) surfaces. These spectra are typical for self-assembled monolayers of long chain alkyls. The dodecanol film displays an asymmetric $CH_2$ stretching frequency of $v_a=2921.6\pm1.0$ $cm^{-1}$ and a symmetric $CH_2$ stretch of $v_s=2852.2\pm1.0$ $cm^{-1}$. The peaks at ~2955 $cm^{-1}$ is the asymmetric CH stretch in the terminal —$CH_3$ group. For the octadocanol film, the asymmetric and symmetric $CH_2$ stretching frequencies are $v_a=2917.7\pm1.0$ $cm^{-1}$ and $v_s=2850.2=1.0$ $cm^{-1}$, respectively.

Figure 7A:
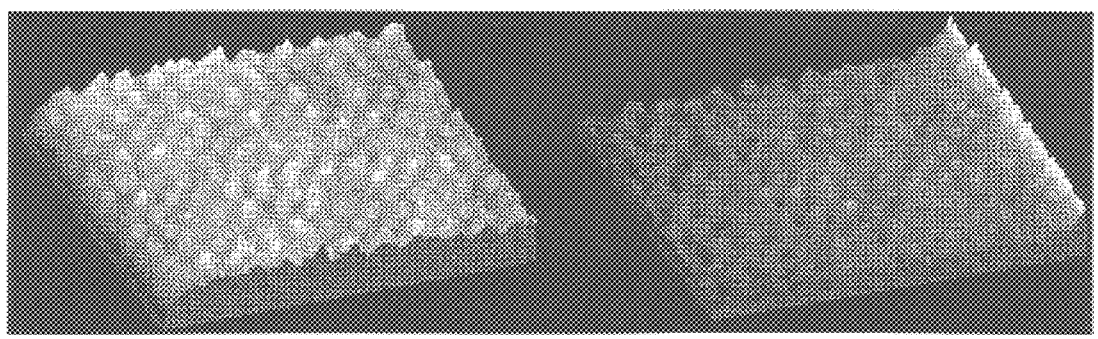
FIG. 7A shows AFM images (55 Å×55 Å) taken in the lateral force mode with no external load for a n-$C_{18}H_{37}$OH assembled Si(100) surface. The two images are from opposite scan directions in the same experiment. A DI Nanoscope III AFM was used.
Figure 7B:
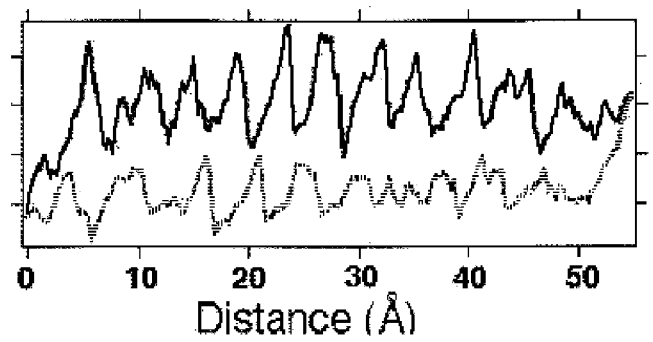
FIG. 7B shows typical line scans from the AFM image in 7A.

Direct evidence for the formation of an ordered monolayer comes from atomic force microscopy (AFM) imaging. FIG. 7A shows AFM lateral force images (55 Å×55 Å) for the C18 assembled Si(100) surface. The two images from opposite scan directions show the well-known friction loop. Lattice resolution is evident in the image, suggesting the presence of molecular order within the SAM. This is particularly obvious when one examines line scans, as shown in FIG. 7B. In each line scan, the lateral force shows regular "stick-slip" features, which are characteristic of an ordered surface [Carpick and Salmeron, *Chem. Rev.* 1997, 97].

Figure 7C:
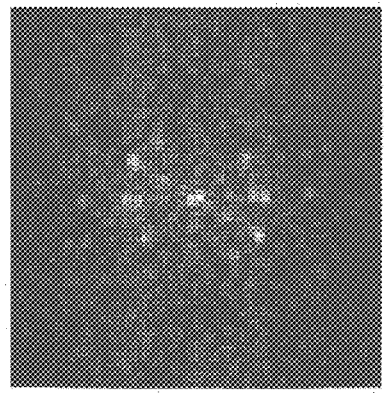
FIG. 7C shows a two-dimensional Fourier transform of the left image in 7A.

Two-dimensional Fourier transform (FIG. 7C) of the image shows six main spots, in addition to some weaker spots. It suggests hexagonal close packing, albeit with significant distortion from the six-fold symmetry. This kind of distortion may result from a number of factors, such as thermal drift, disturbance of the molecular lattice by the AFM tip, or the influence of substrate symmetry. Fourier analysis of several images yields an average lattice parameter, or inter-molecular distance, of 4.8±0.3 Å for the n-$C_{18}H_{37}$O/Si(100) SAM.

The static $H_2O$ contact angle for the SAM coated surface was typically 106–114°. These contact angles are in agreement with those of crystalline —$CH_3$ terminated SAMs.

Characterization of alcohol assembled surfaces after long term (2–4 weeks) exposure to laboratory ambient showed no changes, indicating the chemical stability of the film. FTIR showed little change after the SAM coated surfaces were sonicated in organic solvents such as ether and chloromethanes. However, degradation of the film was observed in boiling water, as revealed by the loss of intensity in FTIR. This was likely a result of hydrolysis. Chemical stability is related to ordering of the surface assembly and should improve with improved film quality.

Figure 12:
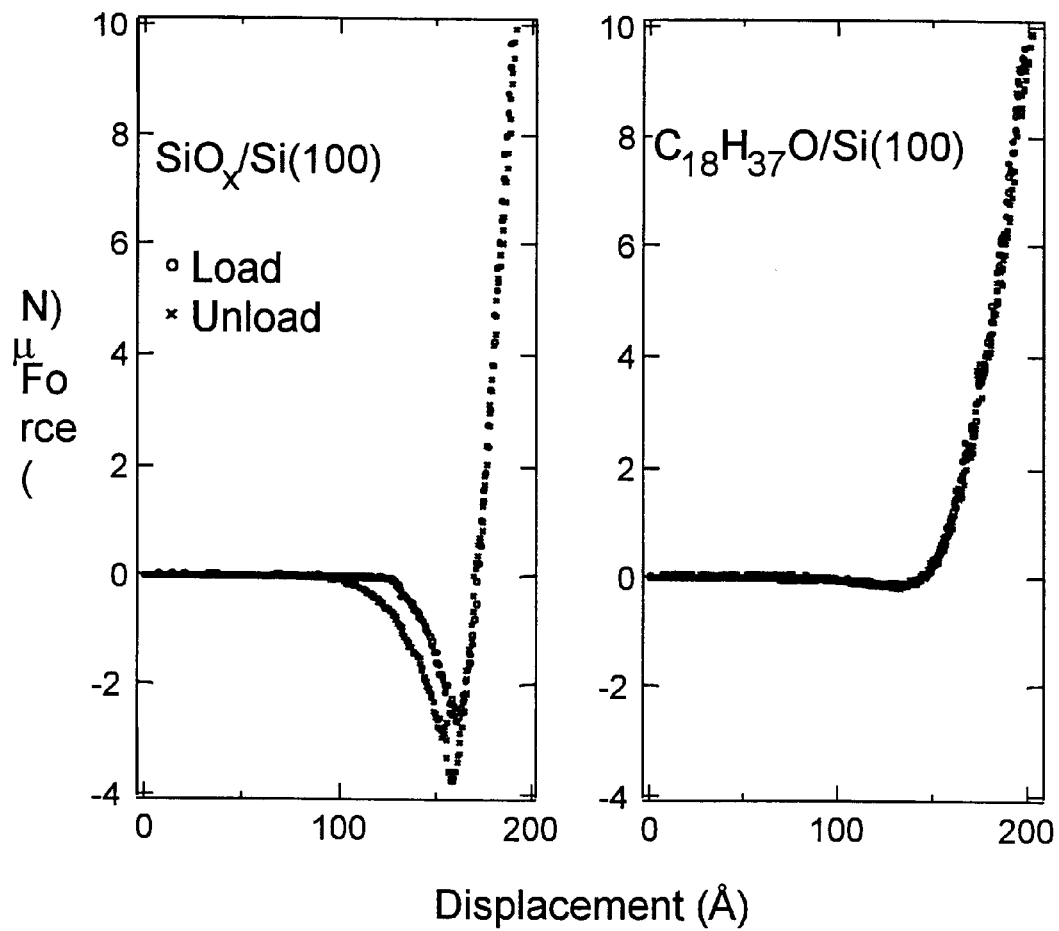
FIG. 12 shows interfacial force microscope (IFM) loading-unloading cycles for native oxide covered Si(100) (left) and octadecanol assembled Si(100) (right).

The SAM coated silicon surfaces also showed good mechanical properties. FIG. 12 compares force profiles between the W tip and the surface for native oxide covered Si(100) (left panel) and octadecanol assembled Si(100) (right panel) using an interfacial force microscope (IFM) [Kiely and Houston, *Langmuir* 1999, 15]. The force profile for the native oxide covered Si(100) showed a very strong attractive interaction well and large hysteresis between loading and unloading. This large attraction well was in part due to a thin water layer present on the oxide surface. In contrast, the SAM coated surface in the left panel showed little attraction (~30 times less than that for the oxide covered surface). More importantly, repeated loading and unloading at the same location showed little change in force profile. This observation establishes the mechanical stability of the molecular layer. For comparison, the same measurement for a monohydride terminated Si surface showed that a large attractive well quickly developed after several loading-unloading cycles.

All the above physical characterizations point to the formation of covalently attached, self-assembled monolayers on silicon surfaces, as suggested by FIG. 2. Unlike well studied thiolate SAMs on Au(111) where both precursor (RSH) and chemisorbed species (RS-Au) are sufficiently mobile, the covalent nature of the silicon surface and the strong anchoring interaction preclude the diffusion of chemisorbed species. An ordered, close-packed SAM on silicon would likely require a sufficient concentration of physisorbed, precursor molecules (ROH) before the anchoring reaction takes place. The high mobility and intermolecular interaction among precursor molecules may lead to an ordered surface assembly.

Figure 13A:
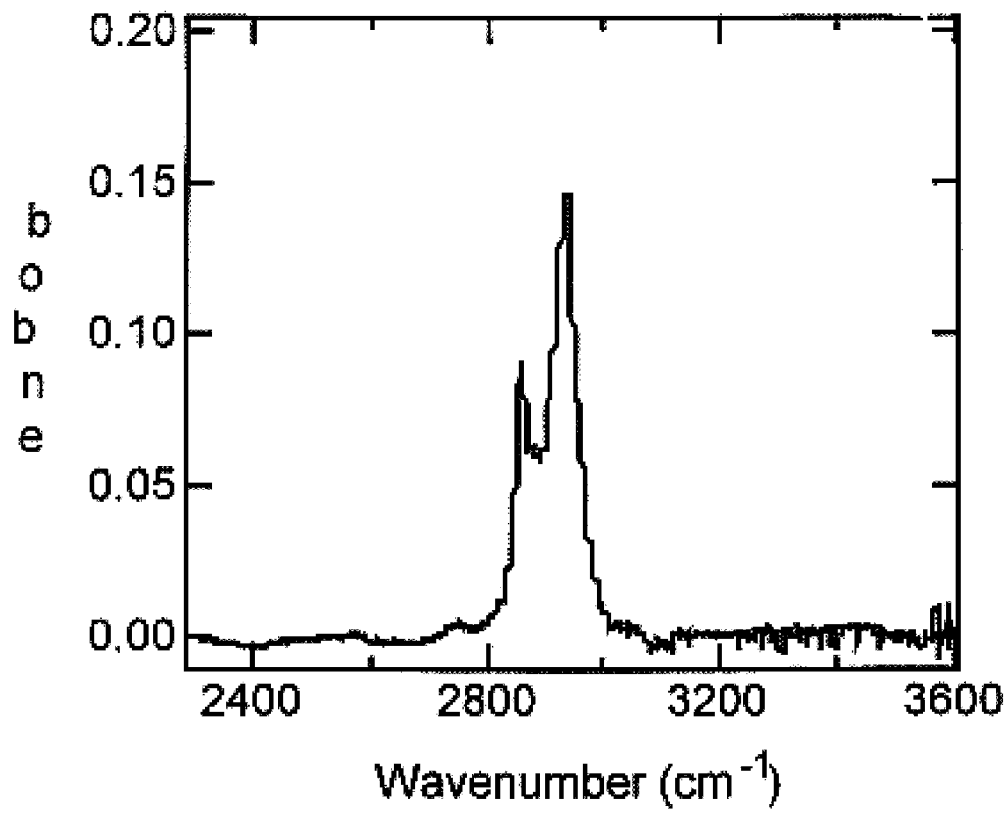
FIG. 13A shows an FTIR spectrum of a molecular assembly of HS—$(CH_2)_{11}$—O—on Si(111).
Figure 13B:
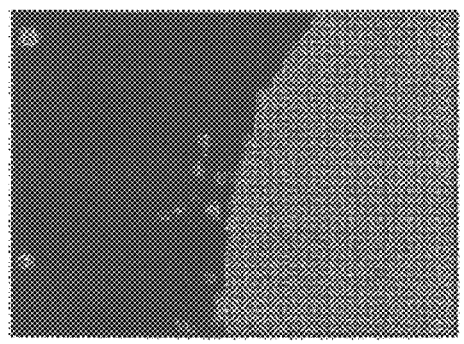
FIG. 13B shows a fluorescence microscope image of TexasRed-tagged maleimide linker molecule covalently attached to the —SH terminated Si(111) surface.

One of the most attractive aspects of surface engineering by SAMs is that surface properties can be tuned by varying the terminal group on the molecule. This kind of molecular level engineering can be used to control surface energy, to introduce reactive surfaces, such as —SH and —$NH_2$, for biomolecular attachment; and to form hydrophobic, hydrophilic or ionic surfaces in microfluidics. FIG. 13A shows an FTIR spectrum of -SH terminated $C_{11}$ alcohol assembled on Si(111). Only symmetric and asymmetric stretches of —$CH_2$— are observed in the spectrum. The functional termination (—SH) of this surface is demonstrated in FIG. 13B, which shows a fluorescence microscope image of Texas-Red tagged maleimide linker molecule covalently attached (gray area in the picture) to the —SH terminated Si(111) surface.

D. Silicon Wafers or "Chips"

The derivitized silicon materials described above can be used to prepare silicon wafers or chips. Such devices have a variety of uses, as described below.

Silicon designs containing channels are advantageously employed because of their adaptability to low cost mass production processes and their ability to incorporate in the fabrication process structural elements that function in fluidic entry and exit from the hybridization site and structures (e.g., electrodes) that may function in hybridization detection. Stable, open-cell materials containing channels between first and second surfaces of the material are used to accomplish enhancements and to introduce qualitatively new features in these devices, whereby the surface area of discrete and isolated binding regions comprising groups of channels is increased by a factor of 100 to 1000 relative to a two-dimensional surface.

The microchip device provides in situ multisite analysis. Silicon materials containing channels are fabricated in oriented arrays with channel diameters selected over the range from 2 nm to several micrometers. Random, interconnected pore arrays also can be made.

Porous silicon is produced most easily through electrochemical etching. It can be processed into two important channel structures, interconnected networks and oriented arrays; The channel diameter is tailored from approximately 2 nm to micrometer dimensions by selection of doping and electrochemical conditions. Etching is thought to proceed through a tunneling mechanism in which electrons are injected into the channel surface through field concentration effects. In the case of p-material the mechanism seems to be through moderation of carrier supply at the electrolyte/silicon interface. In practice, the following structures can be fabricated for use as suitable substrates for the present invention:

i) dense oriented arrays of channels oriented with axis along <100> direction and with channel diameters in the range of 10 to 100 nm. Obtained in p-type material with resistivity less than 10-2 Ω-cm.

ii) dense oriented arrays of channels oriented along <100> direction and with channel diameters in the range less than 10 nm. Obtained in n-type material with resistivity between 10-1 and 10-2 Ω-cm.

iii) dense oriented arrays of rectangular channels oriented with axis along <100> direction, rectangle side defined by {001} planes, and with channel diameters in the range less than 100 nm. Obtained in p-type material with resistivity between 10-1 and 10-2 Ω-cm.

The binding reagents such as DNA probes and oligonucleotides of the present invention may be attached within channels densely packed in a solid substrate, or chip, as shown in FIG. 9.

High channel-density dielectrics which function as molecular sieves are produced by nuclear track etching. While nuclear track etching is used to produce these molecular sieves in a wide range of inorganic materials, it is most often used with dielectrics such as mica and sapphire. In this method, described in U.S. Pat. No. 3,303,085 (Price, et al., which is hereby incorporated by reference in its entirety), a substrate is first bombarded with nuclear particles (typically several MeV alpha particles) to produce disturbances or "tracks" within the normal lattice structure of the material and then wet-etched to produce channels which follow the tracks caused by the nuclear particles. More specifically, Price et al. disclose that the exposure of a mica substrate to heavy, energetic charged particles will result in the formation of a plurality of substantially straight tracks in its lattice structure and that these tracks can be converted into channels by wet etching the substrate.

Channel sizes and density of the channels are variably controllable with channels typically 0.2 $\mu$m in diameter and densities on the order of $10^9/cm^2$, although narrower or broader channels can be generated, leading to greater or smaller channel densities. Particle track depths are energy dependent on the incident particle beam, but resulting channels can be extended, for example, through an entire 500 $\mu$m-thick substrate.

Known microfabrication methods can be used to fabricate manifold structures defining, for instance, integral sample wells that can be used to direct binding reagents or samples towards specific locations on the binding device. A binding device formed from a wafer structure having uniform channels can be bonded to the manifold.

A preferred device in this regard is the silicon array wafer containing channels between first and second surfaces of the wafer, and containing integral sample wells as illustrated in FIG. 8.0. By way of example, this may be constructed as follows: A four inch diameter, 100 $\mu$m thick wafer of crystalline silicon (n-type, doped with $10^{15}$ P/cm$^3$) with axis oriented along <100> direction is coated with photoresist and exposed to light through a mask to define a 50×50 array of 200 $\mu$m square areas having 200 $\mu$m space between them across the 2 cm×2 cm central area of the wafer. The process described by V. Lehmann (J Electrochem. Soc. 140:2836–2843 (1993)) is then used to create patches of closely spaced channels of diameter 2–5 $\mu$m oriented perpendicular to the wafer surface, within each square area defined in the photolithographic step. A 300 $\mu$m thick wafer of silicon dioxide is coated with photoresist and exposed to light through the same mask used to define 200 $\mu$m square channel regions in the silicon wafer, and acid etching is conducted to create 200 $\mu$m square holes in the silicon dioxide wafer. The silicon dioxide wafer is then aligned with and laminated to the silicon wafer using a standard wafer bonding process to form the integral structure shown in the figure. During the high temperature annealing step, the silicon surface of each channel is oxidized to form a layer of silicon dioxide. Similar silicon materials are described in Lehmann et al., Solid State Technology 38:99 (1995); Gruning et al., Applied Physics Letters 68:747 (1996); Lehmann et al., Thin Solid Films 297:13 (1997).

The size of the silicon array wafers may be modified in a variety of ways without departing from the spirit of the invention.

The invention has been disclosed broadly and illustrated in reference to representative embodiments described above. Those skilled in the art will recognize that various modifications can be made to the present invention without departing from the spirit and scope thereof.

What is claimed is:

1. A method for attaching organic molecules to a silicon surface comprising reacting a nucleophilic organic molecule with a halogenated silicon surface, wherein said nucleophilic organic molecule contains a nucleophilic functionality selected from the group consisting of amines, =NH, —OH, —SH, —SeH, —TeH, and —PH$_2$.

2. A method according to claim 1, wherein said silicon surface comprises a silicon selected from the group consisting of crystalline silicon, amorphous silicon, flat silicon, and porous silicon.

3. A method according to claim 1, wherein the reaction of said nucleophilic organic compound with said halogenated silicon surface is performed in solution phase or gas phase.

4. A method according to claim 1, wherein said halogenated silicon surface is prepared by reacting a silicon surface with a halogen source to form a halogenated silicon surface.

5. A method according to claim 4, wherein said silicon surface is prepared by heating a silicon surface to a temperature sufficient to remove impurities from the silicon surface.

6. A method according to claim 4, wherein said halogen source is a chlorine source and said halogenated silicon surface is a chlorinated silicon surface.

7. A method according to claim 6 wherein said chlorine source is selected from the group consisting of Cl$_2$, SO$_2$Cl$_2$, phosgene and oxalyl chloride.

8. A method according to claim 1, wherein said halogenated silicon surface is prepared by reacting a hydrogen terminated silicon surface with a halogen source in gas phase or in solution to form a halogenated silicon surface.

9. A method according to claim 8 wherein said halogen source is a chlorine source and said halogenated silicon surface is a chlorinated silicon surface.

10. A method according to claim 9 wherein said chlorine source is selected from the group consisting of Cl$_2$, SO$_2$Cl$_2$, Cl$_3$CSO$_2$Cl, n-chlorosuccinimide, C$_6$H$_5$Cl$_2$, t-C$_4$H$_9$OCl, PCl$_5$, phosgene and oxalyl chloride.

11. A method according to claim 8 wherein said silicon is reacted with said halogen source in the presence of a radical initiator catalyst, and said reaction is carried out in solution.

12. A method according to claim 11, wherein said catalyst is selected from the group consisting of azocompounds, peroxides, photons, and Bu$_3$SnH.

13. A method according to claim 12, wherein said catalyst is benzoyl peroxide.

14. A method of producing an improved device for detecting multiple binding reactions, comprising reacting an organic molecule containing a nucleophilic functionality with a halogenated silicon surface of said device, wherein said organic molecule is a bifunctional molecule having at least a first functional group and a second functional group, and wherein said first functional group is selected from the group consisting of amines, =NH, —OH, —SH, —SeH, —TeH, and —PH$_2$.

15. The method according to claim 14 wherein said first and second functional groups are selected from —OH and —SH.

16. The method according to claim 14 further comprising linking said bifunctional molecule to a binding reagent selected from the group consisting of DNA, proteins, ligands, and oligonucleotide probes.

17. The method according to claim 16 wherein said bifunctional molecule is linked directly to said binding reagent.

18. The method according to claim 16, wherein said bifunctional molecule is linked to said binding reagent via a second bifunctional spacer molecule.

19. The method according to claim 16 wherein the binding reagents are oligonucleotide probes.

20. The method according to claim 16 wherein the binding reagents are attached within channels in a solid substrate.

* * * * *